United States Patent [19]

Popovich et al.

[11] Patent Number: 4,661,092
[45] Date of Patent: Apr. 28, 1987

[54] PERITONEAL ARTIFICIAL LUNG

[76] Inventors: Robert P. Popovich, 2928 Kassarine Pass, Austin, Tex. 78704; Jack W. Moncrief, 3633 W. Lake, Austin, Tex. 78746

[21] Appl. No.: 559,783

[22] Filed: Dec. 9, 1983

[51] Int. Cl.$^4$ ............................................ A61M 37/00
[52] U.S. Cl. ....................................... 604/26; 422/45; 210/927; 514/667; 514/672
[58] Field of Search .................................. 604/23–33; 128/4, 6, 914; 424/350–353; 422/44–45; 210/927

[56] References Cited

U.S. PATENT DOCUMENTS

| 4,378,797 | 4/1983 | Osterholm | 604/24 |
| 4,443,480 | 5/1984 | Clark, Jr. | 424/352 |
| 4,445,892 | 5/1984 | Hussein et al. | |

OTHER PUBLICATIONS

Renvall et al, "Kinetics of Oxygen in Peritoneal Cavity", Journal of Surgical Research 28, pp. 132–139, (1980).
Creager, *Human Anatomy and Physiology*, Wadsworth, Inc., 1983, p. 541.
A. V. Beran and W. F. Taylor—Peritoneal Dialysis for the Support of Respiratory Insufficiency in Rabbits, (1972) 43, pp. 695–703).
P. J. Collipp, M.D.—Peritoneal Dialysis for the Respiratory Distress Syndrome, Letters to the Journal, JAMA, Jan. 15, 1968, vol. 203, No. 3.
John A. Awad, M.D., Andre Brassard, D.V.M., Ph.D., and Wilfrid M. Caron, M.D., F.R.C.S. (C.), F.A.C.-S.—Intrapertoneal Oxygenation* An Experimental Study in Dogs, International Surgery, Mar. 1970, vol. 53, No. 3, pp. 162–166.
John A. Awad, M.D., Andre Brassard, D.V.M. Ph.D., and Wilfrid M. Caron, M.D., F.A.C.S. (C.), and Camille Cadrin—Intraperitoneal Oxygenation with Hydrogen Peroxide, International Surgery, Oct. 1970, vol. 54, No. 4, pp. 276–282.
Renvall et al., "Intraperitoneal Oxygen and Carbon Dioxide Tensions in Experimental Adhesion Disease and Peritonitis, *The Amer. J. of Surgery*, vol. 130, pp. 286–292, (Sep. 1975).

*Primary Examiner*—John D. Yasko
*Attorney, Agent, or Firm*—Arnold, White & Durkee

[57] ABSTRACT

A process for the treatment of hypoxia is provided. The process involves the infusion of highly oxygenated perfluoro-chemicals into the peritoneal cavity of a patient, for oxygen transport into the body and carbon dioxide transport out of the body. The oxygenated perfluorocarbons are subsequently removed from the peritoneal cavity. The infusion and removal can be on a continuous or intermittent basis.

7 Claims, 2 Drawing Figures

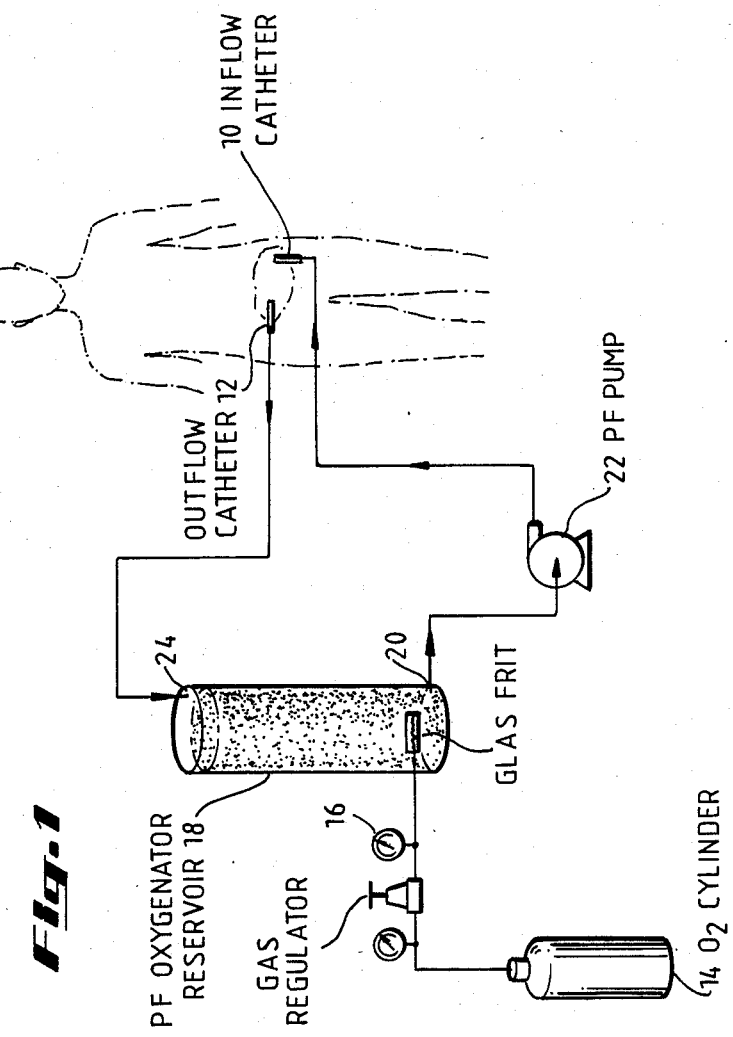

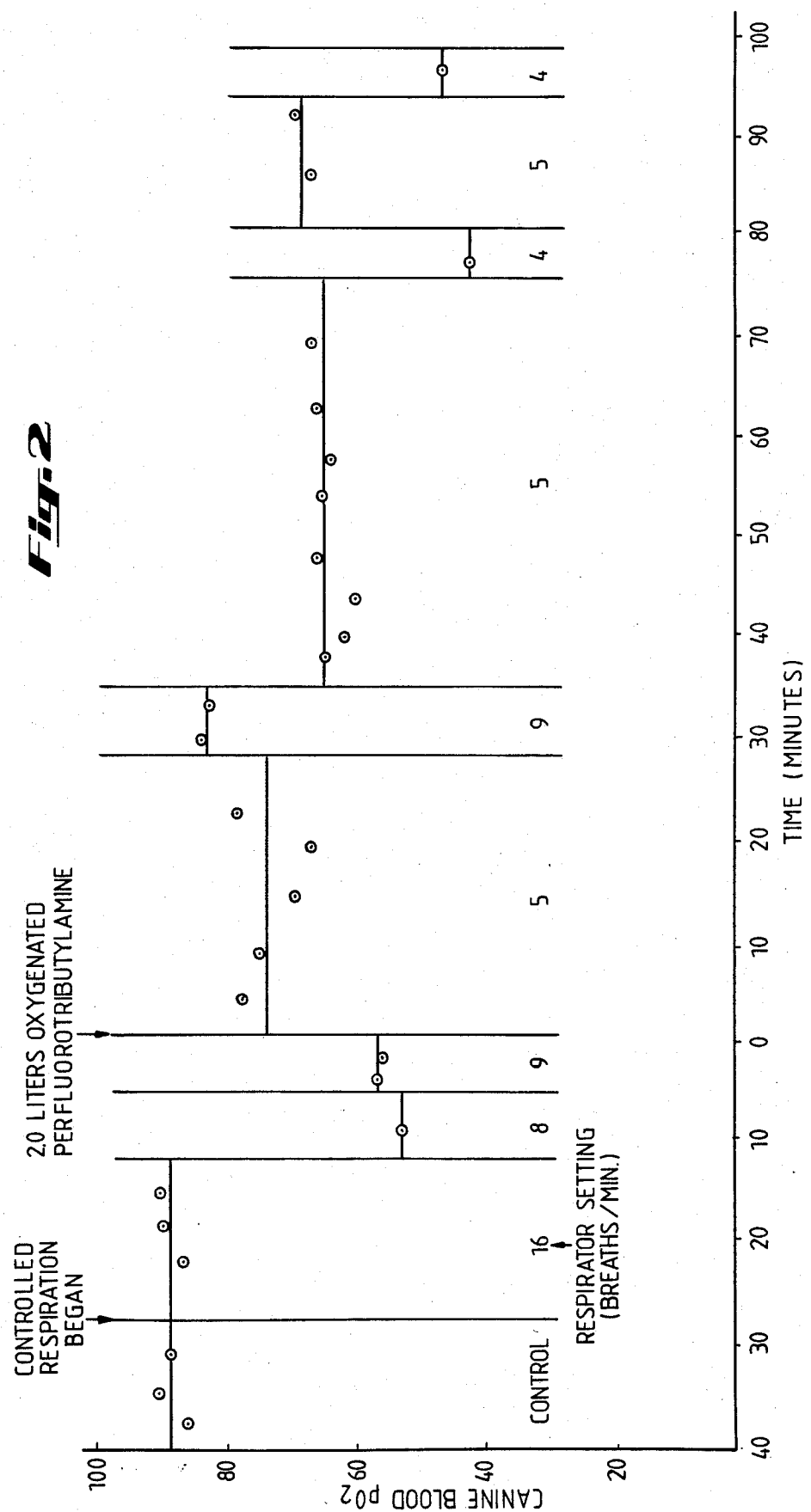

PERITONEAL ARTIFICIAL LUNG

BACKGROUND OF THE INVENTION

Many situations in the practice of clinical medicine produce temporary and reversible lung failure. In this situation, hypoxia, or inadequate oxygenation of the blood may be life threatening or fatal. An incomplete list of the clinical settings in which this might arise includes:

(A) Newborn premature infants
(B) Heart and lung surgery patients
(C) Fulminent pneumonia
(D) Legionnaires disease
(E) Toxic shock syndrome
(F) Severe emphysema
(G) Lung transplants
(H) Adult respiratory distress syndrome
(I) Acute pulmonary embolus The current treatment techniques available for acute life threatening hypoxia include positive pressure ventilation which requires the passage of a per nasal or per oral endotracheal tube, and attachment to a pressure controlled or volume controlled machine ventilator. The problems associated with this procedure include difficulty in initiation, trauma to the nasal or pharyngeal tissue and structures, errors of intubation of the esophagus thus further compromising ventilations; inadvertant intubation of the right main stem bronchus with hyperexpansion of the right lung and collapse or atelectasis of the left lung, damage to the pharynix and vocal cords, on rare occasions erosion through the inominate artery and exanguanation, and not the least, rather extreme discomfort to the patient.

A second form of support in the hypoxic circumstance is with a membrane oxygenator. This is primarily used during a surgical procedure which requires temporary cardiac arrest, such as open heart surgery (i.e. coronary bipass surgery, cardiac valve surgery, and repair of congenital cardiac abnormalities). This procedure requires a highly skilled, well organized team, and can be used for an extremely short period of time, usually for a matter of two to six hours. This procedure produces increasingly severe changes in the blood components, secondary to membrane trauma, hemolysis of red cells, platelet lysis, release of clotting factors, and large volume anticoagulant therapy. All of these may lead to severe tissue toxicity, massive hemorrhage, and cellular destruction if the procedure is not terminated within the time limits stated.

Clearly, an alternative form of tissue and blood oxygenation would be extremely beneficial and, in many of the aforementioned cases, life saving.

SUMMARY OF THE INVENTION

The process of the present invention generally involves the infusion of highly oxygenated perfluorochemicals into the peritoneal cavity with concomitant oxygen transport into the body and carbon dioxide transport out of the body.

In accordance with one embodiment of the process, a source of oxygenated perfluorocarbons is provided in a continuous flow therefrom through the peritoneal cavity of a patient which is established, for oxygen transport into the patients body. To accomodate continuous flow through the peritoneal cavity, there is further provided fluid inflow access to and fluid outflow discharge from the peritoneal cavity of the patient.

Further, fluid inflow access to and fluid outflow discharge from the peritoneal cavity of the patient is established by first and second indwelling catheters adapted to be surgically implanted in the peritoneal cavity of the patient. Also, the source of oxygenated perfluorochemicals may comprise a cylinder of oxygen providing $O_2$ to a perfluorochemical oxygenator reservoir. Continuous flow of oxygenated perfluorochemicals from the reservoir may be by a pump.

In other embodiments of the process, oxygenated perfluorochemicals can be intermittently added to the peritoneal cavity with subsequent drainage following the transport of a portion of the available oxygen.

Accordingly, by the present invention, a process for the treatment of hypoxia is provided which involves infusing oxygenated perfluorochemicals into the peritoneal cavity of a patient, for oxygen transported to the body; and subsequently removing the oxygenated perfluorocarbons from the peritoneal cavity.

BRIEF DESCRIPTION OF THE DRAWINGS

A written description setting forth the best mode presently known for carrying out the present invention, and of the manner of implementing and using it, is provided by a detailed description of illustrative embodiments with reference to the attached drawings wherein:

FIG. 1 is a schematic diagram of apparatus for carrying out the process of the present invention; and FIG. 2 is a plot of the results of a canine experimental study of the process of the present invention.

DETAILED DESCRIPTION

A. Basic Process and Apparatus

The process of the present invention involves the infusion of highly oxygenated perfluorochemicals into the peritoneal cavity of a subject with concomitant oxygen transport into the body and carbon dioxide transport out of the body. The oxygen and carbon dioxide transport occurs through the capillaries of the peritoneal membrane and associated organ systems. The peritoneum is a two square meter, highly vascularized, highly permeable membrane in a closed space in the abdominal region.

Referring to FIG. 1, apparatus for conducting the process is schematically diagrammed. The apparatus includes an inflow catheter 10 to the patient's peritoneal cavity and an outflow catheter 12 therefrom. A cylinder of oxygen 14 provides $O_2$ through gas regulator 16 to perfluorochemical oxygenator reservoir 18. The outlet 20 of oxygenator reservoir 18 is coupled to pump 22. Oxygenated perfluorochemicals are pumped to inflow catheter 10. Outflow catheter 12 is in turn coupled to return inlet 24 of oxygenator reservoir 18. A continuous flow in the circulation loop is established.

B. Experimental Results

A series of experiments was performed to determine the oxygen transportability of the peritoneum utilizing oxygenated perfluorochemicals to determine the clinical efficacy of this process. The clinical protocol included:

(1) Obtain an adult female dog weighing 30-40 pounds.
(2) Implantation of two peritoneal catheters for access to the peritoneal space.
(3) Routine postoperative recovery with catheter maintenance.

(4) Empty the peritoneal cavity of the fluid used for catheter maintenance.
(5) Anesthetize and intubate the canine.
(6) While the animal is breathing spontaneously under light anesthesia, obtain baseline arterial blood gas and respiratory rate measurements.
(7) Inject systemic muscular paralyzing agents and establish ventilatory control by use of a controllable positive pressure respirator.
(8) Adjust the ventilator rate and volume to obtain arterial oxygen and carbon dioxide blood gas concentrations equal to baseline values.
(9) Induce hypoxia by reducing the ventilatory rate while maintaining the ventilatory volume at baseline levels
(10) Alter ventilatory rate with repeated monitoring of blood gases to obtain a comparison with between the effect of the perfluorochemical oxygen transport and blood oxygenation of the peritoneal membrane as compared to ventilator rate effect.

The particular perfluorochemical utilized in the experiments was perfluorotributylamine. Its physiochemical properties are illustrated in Table I below.

TABLE I

PHYSIOCHEMICAL PROPERTIES OF PERFLUOROTRIBUTYLAMINE

* Chemical Formula: $N(C_4F_9)_3$
* Molecular Weight: 671.0
* Oxygen Solubility: 38.4 ml $O_2$/100 ml Solution
* Normal Blood Oxygen Solubility: 20 ml $O_2$/100 ml @$pO_2$=100 mm Hg

EXPERIMENT I

Referring to FIG. 2, there is presented the results of the experimentation with the process of the present invention shown as a plot of blood $pO_2$ versus time. The animal stabilized with a normal oxygen pressure ($pO_2$) of 88 mm Hg with a ventilator rate of 16 breaths per minute with a stroke volume of approximately 250 ml/min. The ventilator rate was then reduced to 8 breaths per minute. The blood arterial $pO_2$ decreased rapidly to approximately 50 mm Hg. This is near the critical level which can induce heart failure so the ventilator rate was increased to 9 breaths per minute. The blood $pO_2$ raised and stabilized at slightly above 50 mm Hg as noted in FIG. 2. At this time 800 ml of fully oxygenated perfluorotributylamine was infused into one of the two peritoneal catheters. The outlet line was then opened and oxygenated perfluorocarbon was pumped through the peritoneal cavity at a rate of approximately 200 ml/min. This resulted in a rapid and sustained raise in the arterial $pO_2$ to approximately 75 mm Hg. Increasing the ventilatory rate to 9 breaths per minute brought the blood $pO_2$ to normal values.

The ventilatory rate was eventually reduced to 4 breaths per minute. This corresponds to only one normal volume breath every 15 seconds. The arterial $pO_2$ fell to approximately 40 mm Hg. Raising the ventilatory rate to 5 breaths per minute again raised the $pO_2$ to approximately the clinically acceptable range of 70 mm Hg. Following a repeat of the 4 breath per minute ventilatory rate the ventilator was turned off (zero breaths per minute) to ascertain if 100% of critical oxygen need can be supplied by this process. This configuration resulted in expiration of the animal. However, the addition of vasoactive agents to increase blood flow to the peritoneal area coupled with a higher flow rate of perfluorocarbons with higher oxygen affinity will increase the oxygen transport rate.

It is apparent that approximately 4.5 breaths per minute with use of perfluorotributylamine results in the same mean blood partial pressure of oxygen as nine breaths per minute without the addition of the peritoneal supplemental oxygen source. This suggests that the peritoneal oxygen uptake rate from the perfluorotributylamine is equivalent to approximately 4.5 breaths per minute. Therefore the oxygen transport rate can be calculated as follows: the percent of normal oxygen requirement provided by the perfluorotributylamine is approximately 4.5 divided by 16, where 16 is the normal ventilatory rate in the anesthetized resting animal, and 4.5 is the number of breaths that can be substituted by the oxygen transport from the alternate perfluorochemical source. This corresponds to 28% of the oxygen supplied by the normal lung. However, a reduction in the ventilatory rate to the severely hypoxic but manageable blood oxygen concentration occurred at nine breaths per minute. Therefore 4.5 breaths per minute substituted by the perfluorocarbons as compared to nine breaths per minute supplied by the lungs in the clinically manageable hypoxic circumstance shows that the perfluorochemicals can supply 50% of the required oxygen to maintain blood oxygenation at clinically acceptable levels.

EXPERIMENT II

A second canine study was performed. In this study the same preparations were performed on a second animal: the animal intubated, anesthetized and paralyzed. The canine was then stabilized at a low arterial oxygen partial pressure and the ventilatory rate and volume maintained at stable levels. The tidal volume of the ventilatory was 200 ml per minute with a respiratory rate of eight cycles per minute. Following stabilization of the animal at hypoxic levels, perfluorotributylamine was intermittently infused and drained from the peritoneal cavity. During the filling phase the flow rate of the perfluorochemical was 162 ml through the abdominal cavity per minute. The results are illustrated in Table II.

TABLE II

RESULTS OF THE SECOND CONTINUOUS FLOW PERFLUOROCARBON CANINE PERITONEAL ARTIFICIAL LUNG STUDY

|  | mean $pO_2$ (mm Hg) |
|---|---|
| Control (Prior to PF) | 42.0 |
| PF Applied | 82.8 |
| Control (PF drained) | 38.3 |
| PF Applied | 80.6 |
| Control (PF drained) | 31.2 |
| PF Applied | 67.3 |
| Control (PF drained) | 35.7 |

The initial arterial $pO_2$ was 42 mm Hg. This rapidly increased to 82.8 mm Hg following infusion of the fully oxygenated perfluorotributylamine. Following complete drainage, the arterial $pO_2$ dropped again to 38.3 mm Hg. Re-infusion of the perfluorotributylamine again raised it to 80.6 mm Hg. Drainage again yielded a $pO_2$ of 31.2 mm Hg. Subsequent perfluorocarbon flow yielded a $pO_2$ of 67.3 mm Hg with a final control value of 35.7 mm Hg following drainage.

A study was then performed to determine the degree of equilibration of perfluorochemicals in the peritoneal cavity in the unanesthetized animal. Highly oxygenated perfluorotributylamine ($pO_2$ of 680 mm Hg) was infused into the peritoneal cavity and allowed to equilibrate for three weeks. Equilibrated arterial oxygen and carbon dioxide partial pressures were 88.9 and 31.0 mm Hg respectively. Venous oxygen and carbon dioxide partial pressures were 29.7 and 59.3 mm Hg, respectively. The equilibrated perfluorocarbon partial pressures were 51.6 mm Hg for oxygen and 36.9 mm Hg for carbon dioxide. This suggests nearly equal transport of oxygen and carbon dioxide from both proximal and distal capillary segments.

At the conclusion of this three week equilibration study, the animal was sacrificed followed by a complete autopsy. No adverse symptoms or changes of any kind were discerned.

The canine oxygen transport studies outlined above support the concept of blood oxygenation at a rate that is clinically efficacious by the instillation of highly oxygenated perfluorocarbons in the peritoneal cavity.

The process can be applied in several ways. A continuous flow of perfluorocarbon can be utilized similar to that outlined above with continuous reoxygenation of the perfluorocarbons. Alternatively, fresh fully oxygenated perfluorocarbon can be intermittently added to the peritoneal cavity with subsequent drainage following the transport of a significant portion of the available oxygen. This method may be preferred if only marginal oxygen transport is indicated and has the advantage of requiring only a single catheter.

Another variation is to infuse the full desired amount of perfluorocarbon with rapid drainage and re-infusion of a portion of the infused volume with repeated oxygenation of the small quantity being recycled.

Alternative perfluorocarbons or other oxygen bearing substances can be utilized with the process. Various methodologies, instrumentation, and catheters can be utilized to deliver the oxygen bearing substances into the peritoneal cavity. Vasoactive agents can be added to enhance oxygen transport via increased blood flow through the peritoneal cavity.

The foregoing description of the invention and experimental studies has been presented for purposes of explanation and illustration. As noted above, many modifications and changes in both method and apparatus may be made without departing from the essence of the invention. It is the applicants' intention in the following claims to cover all such equivalent modifications and variations as fall within the scope of the invention.

What is claimed is:

1. A process for the treatment of hypoxia, comprising the steps of:
   infusing oxygenated perfluorochemicals into the peritoneal cavity of a patient, for oxygen transport into the body; and
   removing the oxygenated perfluorochemicals from the peritoneal cavity.

2. A process for the treatment of hypoxia, comprising the steps of:
   providing a source of oxygenated perfluorochemicals;
   providing fluid inflow access to the peritoneal cavity of a patient;
   providing for fluid outflow discharge from the peritoneal cavity of the patient; and
   establishing a continuous flow of oxygenated perfluorochemicals through the peritoneal cavity of the patient, for oxygen transport into the patient's body.

3. A process for the treatment of hypoxia, comprising the steps of:
   infusing an oxygen-carring substance into the peritoneal cavity of a patient, for oxygen transport into the body; and
   removing the substance from the peritoneal cavity.

4. The process of claim 3 wherein said oxygen-carrying substance has added thereto a vasoactive drug prior to infusion into the peritoneal cavity.

5. A process for the treatment of hypoxia, comprising the steps of:
   providing a source of an oxygen-carring fluid substance;
   providing fluid inflow access to the peritoneal cavity of a patient;
   providing for fluid outflow discharge from the peritoneal cavity of the patient; and
   establishing a continuous flow of the oxygen-carrying fluid substance through the peritoneal cavity of the patient, for oxygen transport into the patient's body.

6. A process for the treatment of hypoxia, comprising the steps of:
   providing an oxygen-carrying substance;
   providing fluid access to the peritoneal cavity of a patient; and
   intermittently infusing into and draining from the peritoneal cavity the oxygen-carrying substance, for providing oxygen transport into the body and carbon dioxide removal from the body.

7. A process for the treatment of hypoxia, which comprises the step of establishing a continuous flow of an oxygen-carrying substance through the peritoneal cavity of a patient, for oxygen transport into the patient's body, using apparatus comprising:
   a first indwelling adapted to be surgically implanted in the peritoneal cavity of a patient to provide a fluid inflow access port;
   a second indwelling catheter adapted to be surgically implanted in the peritoneal cavity of the patient to provide a fluid outflow port;
   a source of oxygenated perfluorochemicals;
   means for establishing circulation of oxygenated perfluorochemicals through the patient's peritoneal cavity from said source via said catheters.

* * * * *

UNITED STATES PATENT AND TRADEMARK OFFICE
CERTIFICATE OF CORRECTION

PATENT NO. : 4,661,092

DATED : April 28, 1987

INVENTOR(S) : Robert P. Popovich and Jack W. Moncrief

It is certified that error appears in the above-identified patent and that said Letters Patent are hereby corrected as shown below:

In the claims, column 6, line 48, after "indwelling"

insert --catheter--.

Signed and Sealed this

Eighteenth Day of August, 1987

Attest:

DONALD J. QUIGG

Attesting Officer

Commissioner of Patents and Trademarks